United States Patent
Koltzenburg et al.

(10) Patent No.: US 7,927,617 B2
(45) Date of Patent: Apr. 19, 2011

(54) PREPARATION COMPRISING AT LEAST ONE CONAZOLE FUNGICIDE

(75) Inventors: Sebastian Koltzenburg, Dannstadt-Schauernheim (DE); Peter Dombo, Wiesbaden (DE); Günter Oetter, Frankenthal (DE); Christian Krüger, Saulheim (DE); Wolfgang Schrof, Neuleiningen (DE); Matthias Bratz, Maxdorf (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 562 days.

(21) Appl. No.: 11/918,522

(22) PCT Filed: Apr. 13, 2006

(86) PCT No.: PCT/EP2006/003429
§ 371 (c)(1),
(2), (4) Date: Oct. 15, 2007

(87) PCT Pub. No.: WO2006/111327
PCT Pub. Date: Oct. 26, 2006

(65) Prior Publication Data
US 2008/0318785 A1   Dec. 25, 2008

(30) Foreign Application Priority Data
Apr. 18, 2005 (DE) .................... 10 2005 017 800

(51) Int. Cl.
*A01N 25/12* (2006.01)
(52) U.S. Cl. ......... 424/409; 424/405; 424/406; 424/417
(58) Field of Classification Search ............... None
See application file for complete search history.

(56) References Cited

U.S. PATENT DOCUMENTS

| | | | |
|---|---|---|---|
| 4,512,969 A | 4/1985 | Chen | |
| 5,787,686 A | 8/1998 | Bott et al. | |
| 6,869,914 B2 * | 3/2005 | Bratz et al. | 504/339 |
| 2003/0118614 A1 * | 6/2003 | Sieverding et al. | 424/400 |
| 2005/0165076 A1 | 7/2005 | Ammermann et al. | |
| 2006/0030486 A1 | 2/2006 | Meyer et al. | |
| 2007/0122436 A1 | 5/2007 | Koltzenburg et al. | |

FOREIGN PATENT DOCUMENTS

| | | |
|---|---|---|
| EP | 0 750 899 A2 | 1/1997 |
| WO | WO-03/055944 A1 | 7/2003 |
| WO | WO-03/073851 A1 | 9/2003 |
| WO | WO-2005/046328 A1 | 5/2005 |

* cited by examiner

Primary Examiner — Neil Levy
(74) Attorney, Agent, or Firm — Birch, Stewart, Kolasch & Birch, LLP

(57) ABSTRACT

The invention relates to preparations, in particular plant-protective preparations which contain a mixture of at least two different active plant-protective substances, wherein a) at least one active substance is selected from a conazole group (active substance 1) and b) another active-plant protective substance (active substance 2) whose water solubility at a temperature of 20° C. is less than 20 g/l., c) at least one type of copolymer CP consisting of M monomers comprising α) at least one type of monoethylenically unsaturated monomer M1 comprising at least one sulphonic acid group and β) at least one type of neutral monoethylenically unsaturated monomer M2, wherein the quantitative ratio between the active substance 1 and the other active plant-protective substance 2 ranges from 1:10 to 10:1. Said invention also relates to novel copolymers CP which are embodied in the form of polymers consisting of at least three types of different monoethylenically unsaturated monomers M and comprise, in the polymerization incorporated form, α) at least one type of monoethylenically unsaturated monomer M1 comprising at least one sulphonic acid group, β1) at least one type of neutral monoethylenically unsaturated monomer M2 whose water solubility at a temperature of 20° C. is less than 30 g/l and β2) at least one type of neutral monoethylenically unsaturated monomer M2b whose water solubility at a temperature of 20° C. is greater than 50 g/l.

22 Claims, No Drawings

PREPARATION COMPRISING AT LEAST ONE CONAZOLE FUNGICIDE

The invention relates to preparations, in particular preparations for crop protection, which comprise at least one conazole fungicide, in particular epoxiconazole, and at least one further active compound.

For application in crop protection and in the protection of materials, it is desirable to formulate fungicidally active compounds in the form of preparations which can easily be diluted with water to the low concentration desired for application. In addition to solvent-containing emulsion concentrates (ECs) in which the active compound is, together with surfactants, dissolved or suspended in an organic solvent or oil which is generally not miscible with water, mention may be made of suspension concentrates (SCs) in which the active compound is present in the form of a finely divided suspension together with surfactants. Also known are water-dispersible powders (WP) and suspoemulsions (SEs) which have at least one first solid active compound phase and at least one further liquid organic phase which is emulsified/suspended in an aqueous phase.

In principle, ECs have the disadvantage that they comprise relatively large amounts of organic solvents which, on the one hand, increases production costs and entails additional risks during storage and handling. Suspension concentrates for their part comprise, in contrast to ECs, only small amounts of volatile organic compounds; however, they have the disadvantage of a lower storage stability, in particular when the active compounds, such as in the case of epoxiconazole, tend to crystallize. Suspoemulsions in turn have, in addition to a content of volatile inflammable organic solvents which cannot be disregarded, the disadvantage that these complex multiphase systems are thermodynamically unstable, so that, on the one hand, the storage stability is frequently unsatisfactory and there may be, or is, an uncontrolled flocculation and formation of a precipitate of organic components on dilution with water.

A further disadvantage of conventional water-dilutable active compound preparations such as SC, EC and SE is the fact that the active compound particles or active compound droplets suspended and emulsified, respectively, in the aqueous phase after dilution of the preparations with water have a relatively large particle size which is generally several μm. However, it is desirable that, after dilution of the formulation with water to the concentration desired for application, the active compound is present in the resulting aqueous preparation in a form which is as finely distributed as possible to ensure, on the one hand, uniform distribution in the formulation and thus better handling and dosing properties and, at the same time, to increase the bioavailability of the active compound in the formulation. Here, formulations in which the heterogeneous phase has mean particle sizes of less than 500 nm are aimed for.

Conazole fungicides are organic active compounds having an imidazole or triazole group whose fungicidal action is, as is known, based on the inhibition of ergosterol biosynthesis and which are therefore active against a number of plant-damaging fungi from the group of the Ascomycetes, Basidiomycetes and Deuteromycetes. Epoxiconazole (common name for rel-1-[[(2R,3S)-3-(2-chlorophenyl)-2-(4-fluorophenyl)oxiranyl]methyl]-1H-1,2,4-triazole), for example, is a more recently discovered active compound from the group of the azole fungicides.

To broaden their activity spectrum and to increase their fungicidal activity, conazole fungicides are frequently formulated together with other active compounds. This may result in problems, in particular if the other active compound only has a low solubility in water.

WO 03/055944 describes the use of copolymers based on acrylamidomethylpropane-sulfonic acid (AMPS) as crystallization inhibitor in aqueous suspension concentrates for crop protection.

The earlier patent application PCT/EP 04/011797 discloses active compound formulations which comprise at least one active compound and at least one random copolymer which can be obtained by free-radical polymerization of olefinically unsaturated sulfonic acids with esters or amides of acrylic acid or of methacrylic acid.

Accordingly, it is an object of the present invention to provide preparations of conazole fungicides and in particular of epoxiconazole which are dispersible in water or can be easily diluted with water without undesirable separations taking place. The preparations should comprise the smallest possible amounts of organic solvents and also ensure that the active compound is finely distributed in the aqueous phase on dilution. Also desirable is high storage stability.

This object is achieved by a preparation which, in addition to at least one conazole fungicide (active compound 1), comprises at least one further crop protection agent 2 which has a solubility in water at 20° C. of less than 20 g/l, and at least one copolymer CP constructed of ethylenically unsaturated monomers M, where the monomers M constituting the copolymer CP comprise α) at least one monoethylenically unsaturated monomer M1 which has at least one sulfonic acid group, and β) at least one neutral monoethylenically unsaturated monomer M2, where the ratio of active compound 1 to the at least one further crop protection agent 2 is in the range from 1:10 to 10:1.

Accordingly, the invention relates to preparations comprising a mixture of at least two different crop protection agents, where a) at least one active compound is selected from the group of the conazoles (active compound 1) and b) the at least one further crop protection agent (active compound 2) has a solubility in water at 20° C. of less than 20 g/l, furthermore comprising c) at least one copolymer CP constructed of ethylenically unsaturated monomers M, where the monomers M comprise α) at least one monoethylenically unsaturated monomer M1 which has at least one sulfonic acid group, and β) at least one neutral monoethylenically unsaturated monomer M2, where the ratio of active compound 1 to the at least one further crop protection agent 2 is in the range from 1:10 to 10:1.

In an advantageous manner, the preparations according to the invention are suitable for stabilizing mixtures of at least one conazole fungicide, in particular epoxiconazole, and the active compound 2 in aqueous phase without any organic solvents being required. In contrast to the suspoemulsions described in the prior art, dilution of the preparations according to the invention with water affords aqueous formulations in which epoxiconazole and the at least one further active compound 2 are present in extremely finely divided or even molecularly dispersed form in the continuous aqueous phase. It is assumed that the active compounds form aggregates with the copolymers CP in the aqueous phase. These aggregates generally have mean particle sizes of less than 500 nm, in particular less than 400 nm, especially less than 300 nm and very especially less than 200 nm. On dilution of the preparation according to the invention, there are very few, if any, inhomogeneities and instabilities as a result of coagulation, crystallization, flocculation or sedimentation. In addition, presumably by virtue of the extremely fine division of the active compounds in the aqueous application form, corresponding to the very low apparent particle diameter of the active compound aggregates, the activity of the active compounds is increased compared to conventional formulations of azole fungicides and in particular of epoxiconazole.

The stated particle sizes are weight-average particle sizes which can be determined by dynamic light scattering. The person skilled in the art is familiar with methods to achieve this, for example from H. Wiese in D. Distler, Wässrige Polymerdispersionen [Aqueous polymer dispersions], Wiley-VCH 1999, chapter 4.2.1, p. 40ff and literature cited therein, and also H. Auweter, D. Horn, J. Colloid Interf. Sci. 105 (1985) 399, D. Lilge, D. Horn, Colloid Polym. Sci. 269 (1991) 704 or H. Wiese, D. Horn, J. Chem. Phys. 94 (1991) 6429.

As active compound 1, the preparations according to the invention comprise at least one conazole fungicide (see http://www.hclrss.demon.co.uk/class_fungicides.html). As is known, the conazole fungicides include certain imidazole compounds, such as climbazole, clotrimazole, imazalil, oxpoconazole, prochloraz, and triflumizole, and also certain triazole compounds, such as azaconazole, bromuconazole, cyproconazole, dichlobutrazole, difenoconazole, diniconazole, epoxiconazole, etaconazole, fenbuconazole, fluquinconazole, flusilazole, flutriafol, furconazole, hexaconazole, imibenconazole, ipconazole, metconazole, myclobutanil, penconazole, propiconazole, prothioconazole, quinconazole, simeconazole, tebuconazole, tetraconazole, triticonazole, triadimefone, triadimenole and uniconazole. The active compound 1 is in particular one of the abovementioned triazole compounds, especially cyproconazole, epoxiconazole, fluquinconazole, hexaconazole, metconazole, penconazole, propiconazole, prothioconazole, tebuconazole and triticonazole. In a particularly preferred embodiment, the active compound 1 is epoxiconazole. In another particularly preferred embodiment the active compound 1 is metconazole.

Furthermore, the active compound preparations according to the invention comprise at least one, for example 1 or 2, further active compounds 2 which have a solubility in water at 20° C. of less than 20 g/l, in particular less than 10 g/l and especially less than 5 g/l. The active compounds 2 are in particular fungicidally active compounds. However, in principle, they can also be active compounds different from fungicides, for example insecticides, acaricides, herbicides, nematicides or growth regulators. What is essential is that active compound 1 and active compound 2 are different, that at least one of the active compounds is a conazole fungicide and that the further active compound has a solubility in water at 20° C. of less than 20 g/l. Suitable active compounds 2 are known to the person skilled in the art; see, for example, http://www.hclrss.demon.co.uk/index.html.

In a preferred embodiment of the invention, the active compound 2 has a melting point of less than 70° C. (at atmospheric pressure).

Examples of fungicidally active compounds 2 which are preferred according to the invention are, for example,
 strobilurin fungicides, such as azoxystrobin, dimoxystrobin, fluoxastrobin, kresoxim-methyl, metominostrobin, orysastrobin, picoxystrobin, pyraclostrobin and trifloxystrobin, in particular pyraclostrobin,
 morpholine fungicides, such as aldamorph, benzamorf, carbamorph, dodemorph, dimethomorph, fenpropimorph, fenpropidin, flumorph and tridemorph,
 chlorothalonil,
 boscalid,
 nonclassified fungicides selected from the group consisting of spiroxamine and metrafenone,
 and the abovementioned conazole fungicides different from the active compound 1 present in the composition, in particular prochloraz, cyproconazole, fluquinconazole, hexaconazole, metconazole, penconazole, propiconazole, prothioconazole, tebuconazole and triticonazole and especially metconazole, fluquinconazole and prothioconazole.

In a particularly preferred embodiment, the active compound 2 is pyraclostrobin. In a further particularly preferred embodiment, the active compound 2 is one of the abovementioned conazole fungicides, in particular prochloraz, cyproconazole, fluquinconazole, hexaconazole, metconazole, penconazole, propiconazole, prothioconazole, tebuconazole and triticonazole and especially metconazole, fluquinconazole and prothioconazole.

Especially, active compounds 1 and 2 are a combination of epoxiconazole as active compound 1 with at least one strobilurin, in particular pyraclostrobin, and, if appropriate, one further active compound, for example fenpropidin as active compound(s)2, or a combination of epoxiconazole as active compound 1 with at least one further conazole fungicide different from epoxiconazole as active compound 2, in particular a conazole fungicide selected from the group consisting of prochloraz, cyproconazole, fluquinconazole, hexaconazole, metconazole, penconazole, propiconazole, prothioconazole, tebuconazole and triticonazole and especially metconazole, fluquinconazole and prothioconazole.

A further preferred embodiment relates to preparations which comprise metconazole as active compound 1 and a strobilurin, in particular pyraclostrobin, as active compound 2.

In the preparations according to the invention, the ratio of conazole fungicide to the at least one further active compound 2 is preferably in the range from 1:8 to 8:1, in particular in the range from 5:1 to 1:5 and especially in the range from 1:3 to 3:1.

According to the invention, the preparations comprise at least one copolymer CP which stabilizes the active compound in the aqueous phase. In general, the preparations according to the invention comprise the copolymer CP in an amount from 0.1 to 10 parts by weight, in particular from 0.5 to 8 parts by weight, especially from 1 to 5 parts by weight, based on 1 part by weight of the total amount of active compounds, i.e. the total amount of active compound 1 and active compound 2 (corresponds to 10 to 1000% by weight, based on the total amount of active compound 1 and active compound 2).

The copolymers CP are generally so-called random copolymers, i.e. the monomers M1 and M2 are distributed in a random fashion along the polymer chain. In principle, alternating copolymers CP and block copolymers CP are also suitable.

According to the invention, the monomers M constituting the copolymer CP comprise at least one monoethylenically unsaturated monomer M1 having at least one sulfonic acid group. The proportion of monomers M1 in the monomers M is generally from 1 to 90% by weight, frequently from 1 to 80% by weight, in particular from 2 to 70% by weight and especially from 5 to 60% by weight, based on the total amount of monomers M.

Suitable monomers M1 are, in principle, all monoethylenically unsaturated monomers having at least one sulfonic acid group. The monomers M1 may be present both in their acid form and in the salt form. The stated parts by weight refer to the acid form.

Examples of monomers M1 are styrenesulfonic acid, vinylsulfonic acid, allylsulfonic acid, methallylsulfonic acid, and also the monomers defined by formula I below, and the salts of the abovementioned monomers 1.

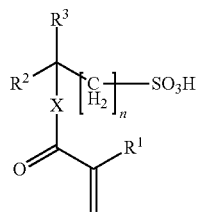

In formula I:
n is 0, 1, 2 or 3, in particular 1 or 2;
X is O or $NR^5$;
$R^1$ is hydrogen or methyl;
$R^2$, $R^3$ independently of one another are hydrogen or $C_1$-$C_4$-alkyl, in particular hydrogen or methyl, and
$R^5$ is hydrogen or $C_1$-$C_4$-alkyl, in particular hydrogen.

Examples of monomers M1 of formula I are 2-acrylamido-2-methylpropanesulfonic acid, 2-methacrylamido-2-methylpropanesulfonic acid, 2-acrylamidoethanesulfonic acid, 2-methacrylamidoethanesulfonic acid, 2-acryloxyethanesulfonic acid, 2-methacryloxyethanesulfonic acid, 3-acryloxypropanesulfonic acid and 2-methacryloxypropanesulfonic acid.

If the monomers M1 are present in their salt form, they have a corresponding cation as counterion. Examples of suitable cations are alkali metal cations, such as $Na^+$ or $K^+$, alkaline earth metal ions, such as $Ca^{2+}$ and $Mg^{2+}$, furthermore ammonium ions, such as $NH_4^+$, tetraalkylammonium cations, such as tetramethylammonium, tetraethylammonium and tetrabutylammonium, furthermore protonated primary, secondary and tertiary amines, in particular those carrying 1, 2 or 3 radicals selected from the group consisting of $C_1$-$C_{20}$-alkyl groups and hydroxyethyl groups, for example the protonated forms of mono-, di- and tributylamine, propylamine, diisopropylamine, hexylamine, dodecylamine, oleylamine, stearylamine, ethoxylated oleylamine, ethoxylated stearylamine, ethanolamine, diethanolamine, triethanolamine or of N,N-dimethylethanolamine.

In addition to the monomers M1, the monomers M constituting the copolymer CP comprise at least one neutral monoethylenically unsaturated monomer M2. Neutral means that the monomers M2 have no functional group which is present in ionic form or reacts acidic or basic in aqueous medium. The total amount of the monomers M2 is generally from 10 to 99% by weight, frequently from 20 to 99% by weight, in particular from 30 to 98% by weight and especially from 40 to 95% by weight, based on the total weight of the monomers M.

Examples of monomers M2 are those with limited solubility in water, for example a solubility in water of less than 50 g/l and in particular less than 30 g/l (at 20° C. and 1013 mbar) and those having an increased solubility in water, for example a solubility in water of $\geq$50 g/l, in particular $\geq$80 g/l (at 20° C. and 1013 mbar). Hereinbelow, monomers having limited solubility in water are also referred to as monomers M2a. Hereinbelow, monomers having increased solubility in water are also referred to as monomers M2b.

Examples of monomers M2a are vinylaromatic monomers, such as styrene and styrene derivatives, such as α-methylstyrene, vinyltoluene, ortho-, meta- and para-methylstyrene, ethylvinylbenzene, vinylnaphthalene, vinylxylene, and also the corresponding halogenated vinylaromatic monomers, α-olefins having 2 to 12 carbon atoms, such as ethene, propene, 1-butene, 1-pentene, 1-hexene, isobutene, diisobutene and the like, dienes, such as butadiene and isoprene, vinyl esters of aliphatic $C_1$-$C_{18}$-carboxylic acids, such as vinyl acetate, vinyl propionate, vinyl laurate and vinyl stearate, vinyl halides, such as vinyl chloride, vinyl fluoride, vinylidene chloride, vinylidene fluoride, mono- and di-$C_1$-$C_{24}$-alkyl esters of monoethylenically unsaturated mono- and dicarboxylic acids, for example of acrylic acid, of methacrylic acid, of fumaric acid, of maleic acid or of itaconic acid, mono- and di-$C_5$-$C_{12}$-cycloalkyl esters of the abovementioned monoethylenically unsaturated mono- and dicarboxylic acids, mono- and diesters of the abovementioned monoethylenically unsaturated mono- and dicarboxylic acids with phenyl-$C_1$-$C_4$-alkanols or phenoxy-$C_1$-$C_4$-alkanols, furthermore monoethylenically unsaturated ethers, in particular $C_1$-$C_{20}$-alkyl vinyl ethers, such as ethyl vinyl ether, methyl vinyl ether, n-butyl vinyl ether, octadecyl vinyl ether, triethylene glycol vinyl methyl ether, vinyl isobutyl ether, vinyl 2-ethylhexyl ether, vinyl propyl ether, vinyl isopropyl ether, vinyl dodecyl ether, vinyl tert-butyl ether.

The monomers M2a are preferably selected from the group consisting of vinylaromatic monomers, esters of acrylic acid with $C_2$-$C_{20}$-alkanols, in particular $C_2$-$C_{10}$-alkanols, such as ethyl acrylate, n-butyl acrylate, 2-butyl acrylate, isobutyl acrylate, tert-butyl acrylate, 2-ethylhexyl acrylate, decyl acrylate, lauryl acrylate and stearyl acrylate, esters of acrylic acid with $C_4$-$C_{10}$-cycloalkanols, such as cyclohexyl acrylate, esters of acrylic acid with phenyl-$C_1$-$C_4$-alkanols, such as benzyl acrylate, 2-phenylethyl acrylate and 1-phenylethyl acrylate, esters of acrylic acid with phenoxy-$C_1$-$C_4$-alkanols, such as 2-phenoxyethyl acrylate, the esters of methacrylic acid with $C_1$-$C_{20}$-alkanols, preferably $C_1$-$C_{10}$-alkanols, in particular with $C_1$-$C_6$-alkanols, such as methyl methacrylate, ethyl methacrylate, n-butyl methacrylate, 2-butyl methacrylate, isobutyl methacrylate, tert-butyl methacrylate, 2-ethylhexyl methacrylate, decyl methacrylate, lauryl methacrylate and stearyl methacrylate, esters of methacrylic acid with $C_4$-$C_{10}$-cycloalkanols, such as cyclohexyl methacrylate, esters of methacrylic acid with phenyl-$C_1$-$C_4$-alkanols, such as benzyl methacrylate, 2-phenylethyl methacrylate and 1-phenylethyl methacrylate, and esters of methacrylic acid with phenoxy-$C_1$-$C_4$-alkanols, such as 2-phenoxyethyl methacrylate. In a particularly preferred embodiment, the monomers M2a comprise at least 80%, based on the total amount of the monomers M2a, and in particular exclusively esters of acrylic acid and/or methacrylic acid with $C_1$-$C_6$-alkanols.

Neutral monoethylenically unsaturated monomers having increased solubility in water or even water miscibility are known to the person skilled in the art, for example from Ullmann's Encyclopedia of Industrial Chemistry, "Polyacrylates", 5th ed. on CD-ROM, Wiley-VCH, Weinheim 1997. Typical monomers M2b are hydroxy-$C_2$-$C_4$-alkyl esters of monoethylenically unsaturated monocarboxylic acids, in particular of acrylic acid and of methacrylic acid, such as 2-hydroxyethyl acrylate, 2-hydroxypropyl acrylate, 3-hydroxypropyl acrylate, 2-hydroxybutyl acrylate, 4-hydroxybutyl acrylate, 2-hydroxyethyl methacrylate, 2-hydroxypropyl methacrylate, 3-hydroxypropyl methacrylate, 2-hydroxybutyl methacrylate, 4-hydroxybutyl methacrylate, furthermore amides of monoethylenically unsaturated monocarboxylic acids, such as acrylamide, methacrylamide, furthermore acrylonitrile and methacrylonitrile, N-vinyllactams, such as N-vinylpyrrolidone, N-vinylcaprolactam, N-vinylamides of aliphatic $C_1$-$C_4$-monocarboxylic acids, such as N-vinylformamide, N-vinylacetamide, monoethylenically unsaturated monomers which carry urea groups, such as N-vinyl- and N-allylurea, and also derivatives of imidazolidin-2-one, for example N-vinyl- and N-allylimidazolidin-2-one, N-vinyloxyethylimidazolidin-2-one, N-allyloxyethylimidazolidin-2-one, N-(2-acrylamidoethyl)imidazolidin-2-one, N-(2-acryloxyethyl)imidazolidin-2-one, N-(2-methacrylamidoethyl)imidazolidin-2-one, N-(2-methacryloxyethyl)imidazolidin-2-one (=ureido methacrylate), N-[2-(acryloxyacetamido)ethyl]imidazolidin-2-one, N-[2-(2-acryloxyacetamido)ethyl]imidazolidin-2-one, N-[2-(2-methacryloxyacetamido)ethyl]-imidazolidin-2-one; and the like. The monomers M2b are preferably selected from hydroxy-$C_1$-$C_4$-alkyl esters of acrylic acid and of methacrylic acid, acrylamide, methacrylamide, acrylonitrile, N-vinyllactams, and particular preference is given to the hydroxy-$C_2$-$C_4$-alkyl esters of acrylic acid and of methacrylic acid. In particular, the monomers M2b comprise at least 80% by weight, based on the total amount of monomers M2b, of at least one hydroxy-$C_2$-$C_4$-alkyl ester of acrylic acid and/or of methacrylic acid.

The monomers M2 preferably comprise at least one of the abovementioned monomers M2a having a solubility in water at 20° C. of less than 50 g/l and in particular less than 30 g/l. The proportion of monomers M2a in the monomers M constituting the copolymer CP is typically in the range from 10 to 99% by weight, frequently in the range from 20 to 99% by weight, in particular in the range from 30 to 98% by weight and especially in the range from 40 to 95% by weight, based on the total weight of monomers M.

In a further preferred embodiment, the monomers M2 are selected from the group consisting of methyl acrylate and mixtures of methyl acrylate with the monomers M2a and/or M2b mentioned above. Here, the amount of methyl acrylate or the mixture of methyl methacrylate with the monomers M2b is typically from 10 to 99% by weight, in particular from 20 to 98% by weight and especially from 40 to 95% by weight of the total amount of monomers.

In a first preferred embodiment of the invention, the monomer M2a is the only or almost the only monomer M2 and makes up at least 95% by weight and in particular at least 99% by weight of the monomers M2.

A specific aspect of the first embodiment relates to preparations in which the copolymer CP comprises as monomer M2a at least one first monoethylenically unsaturated monomer M2a(1) and at least one monomer M2a(2) different therefrom. The monomers M2a(1) are monomers having a solubility in water at 20° C. and 1013 mbar of from 1 to <50 g/l, in particular from 5 to 30 g/l. Preferred monomers M2a(1) are $C_2$-$C_4$-alkyl acrylates and $C_1$-$C_4$-alkyl methacrylates, in particular methyl methacrylate, ethyl acrylate, ethyl methacrylate, n-propyl acrylate, especially methyl methacrylate. The monomers M2a(2) are monoethylenically unsaturated monomers having a solubility in water at 20° C. and 1013 mbar of less than 1 g/l, in particular less than 0.5 g/l. Preferred monomers M2a(2) are the esters of acrylic acid and methacrylic acid with $C_6$-$C_{20}$-alkanols, in particular with $C_8$-$C_{18}$-alkanols, such as n-octyl acrylate, n-octyl methacrylate, decyl acrylate, decyl methacrylate, lauryl acrylate, lauryl methacrylate, myristyl acrylate, myristyl methacrylate, cetyl acrylate, cetyl methacrylate, stearyl acrylate and stearyl methacrylate. The amount of monomers M2a(1), based on the total amount of monomers M, is generally from 10 to 98% by weight, in particular from 20 to 90% by weight. The amount of monomers M2a(2), based on the total amount of monomers M, is generally from 1 to 89% by weight, in particular from 5 to 60% by weight. In this embodiment, the amount of monomers M1 is generally from 1 to 89% by weight, in particular from 5 to 60% by weight, based on the total amount of monomers M.

In a second preferred embodiment of the invention, the monomers M2 comprise, in addition to the monomer M2a, at least one monomer M2b which has a solubility in water at 20° C. of at least 50 g/l and in particular at least 80 g/l. Correspondingly, the monomers M which constitute the copolymer CP comprise, in addition to the monomer M1, both at least one of the abovementioned monomers M2a, in particular at least one of the monomers M2a mentioned as being preferred, and at least one of the abovementioned monomers M2b, in particular at least one of the monomers M2b mentioned as being preferred. Such copolymers are novel and also form part of the subject matter of the present invention.

Frequently, the total amount of monomers M1+M2b will not exceed 90% by weight, in particular 80% by weight and especially 70% by weight, based on the total amount of monomers M, and is, in particular, in the range from 10 to 90% by weight, in particular in the range from 20 to 80% by weight and especially in the range from 30 to 70% by weight, based on the total amount of monomers M. Correspondingly, the monomers M2a frequently make up at least 10% by weight, in particular at least 20% by weight and especially at least 30% by weight, for example from 10 to 90% by weight, in particular from 20 to 80% by weight and especially from 30 to 70% by weight, based on the total amount of monomers M.

In this second particularly preferred embodiment, the monomers M1 preferably make up from 1 to 80% by weight, in particular from 2 to 70% by weight and particularly preferably from 5 to 60% by weight, the monomers M2a preferably make up from 10 to 90% by weight; in particular from 20 to 80% by weight and particularly preferably from 30 to 70% by weight and the monomers M2b preferably make up from 5 to 89% by weight, in particular from 10 to 78% by weight and particularly preferably from 20 to 65% by weight, based on the total amount of monomers M. Among these, particular preference is given to copolymers CP whose constituting monomers M comprise as monomers M1 at least one monomer of the formula I, as monomers M2a at least one monomer selected from the group consisting of esters of acrylic acid with $C_2$-$C_{10}$-alkanols and esters of methacrylic acid with $C_1$-$C_{10}$-alkanols and as monomers M2b at least one monomer selected from the group consisting of hydroxy-$C_2$-$C_4$-alkyl esters of acrylic acid and of methacrylic acid.

In a third preferred embodiment of the invention, the monomers constituting the copolymer CP comprise, as monomers M2, methyl acrylate or a mixture of methyl acrylate with at least one of the abovementioned monomers M2b. The amount of monomers M1, based on the total amount of monomers, is in the ranges mentioned above and is generally from 1 to 90% by weight, in particular from 2 to 80% by weight and especially from 5 to 60% by weight. The total amount of methyl acrylate and any monomers M2b employed is generally from 10 to 99% by weight, in particular from 20 to 98% by weight and especially from 40 to 95% by weight, based on the total amount of monomers M. With respect to preferred monomers M2b, what was said above applies. In mixtures of methyl acrylate with monomers M2b, the weight ratio of methyl acrylate:monomer M2b is typically in the range from 10:1 to 1:1, in particular from 5:1 to 1.2:1.

In addition, the monomers M constituting the copolymer may comprise further monomers M3 different from the monomers M1 and M2. The proportion of monomers M3 in the total amount of monomers M is preferably not more than 40% by weight, in particular not more than 20% by weight. In a preferred embodiment, the monomers comprise no or not more than 3% by weight, especially not more than 1% by weight, of monomers M3 different from the monomers M1 and M2.

The monomers M3 include monoethylenically unsaturated monomers having at least one carboxylic acid group, in particular monoethylenically unsaturated mono- and dicarboxylic acids having 3 to 6 carbon atoms (monomers M3a), such as acrylic acid, methacrylic acid, vinylacetic acid, crotonic acid, fumaric acid, maleic acid, itaconic acid and the like, and the anhydrides of the abovementioned monoethylenically unsaturated dicarboxylic acids, where the proportion of monomers M3a does generally not exceed 20% by weight and in particular 10% by weight, based on the total amount of monomers M.

The monomers M3 furthermore include polyethylenically unsaturated monomers (M3b). The proportion of such monomers M3 will generally not be more than 2% by weight and in particular hot more than 0.5% by weight, based on the total amount of monomers M. Examples of these are vinyl and allyl esters of monoethylenically unsaturated carboxylic acids, such as allyl acrylate and allyl methacrylate, di- and polyacrylates of di- or polyols, such as ethylene glycol diacrylate, ethylene glycol dimethacrylate, butanediol diacrylate, butanediol dimethacrylate, hexanediol diacrylate, hexanediol dimethacrylate, triethylene glycol diacrylate, triethylene glycol trimethacrylate, tris(hydroxymethyl)ethane triacrylate and tris(hydroxymethyl)ethane trimethacrylate, pentaerythritol triacrylate and pentaerythritol trimethacrylate, further the allyl and methallyl esters of polyhydric carboxylic acids, such as diallyl maleate, diallyl fumarate, diallyl phthalate. Typical monomers M3b also include compounds such as divinylbenzene, divinylurea, diallylurea, triallyl cyanurate, N,N'-divinyl- and N,N'-diallylimidazolidin-2-one, and also methylenebisacrylamide and methylenebismethacrylamide.

For the preparations according to the invention, preference is furthermore given to copolymers CP having a number-average molecular weight $M_n$ in the range from 1000 to 500 000 Dalton, frequently in the range from 1500 to 100 000 Dalton, in particular from 2000 to 50 000 Dalton and especially from 5000 to 20 000 Dalton. Frequently, the weight-average molecular weight is in the range from 2000 to 1 000 000 Dalton, frequently in the range from 3000 to 200 000 Dalton, in particular from 4000 to 100 000 Dalton and especially from 10 000 to 50 000 Dalton. The ratio $M_w/M_n$ is frequently in the range from 1.1:1 to 10:1, in particular in the range from 1.2:1 to 5:1. The molar masses $M_w$ and $M_n$ and the nonuniformity of the polymers are determined by size exclusion chromatography (=gel permeation chromatography or short GPC). Commercial polymethyl methacrylate (PMMA) calibration sets can be used as calibration material.

In general, the copolymer comprised in the preparations according to the invention will have a glass transition temperature $T_g$ in the range from −80 to 160° C. and frequently in the range from −40 to +100° C. Here, the glass transition temperature $T_g$ is to be understood as meaning the "midpoint temperature" determined according to ASTM D 3418-82 by differential thermal analysis (DSC) (cf. Ullmann's Encyclopedia of Industrial Chemistry, 5th Edition, Volume A 21, VCH Weinheim 1992, p. 169 and also Zosel, Farbe und Lack 82 (1976), pp. 125-134, see also DIN 53765).

In this context, it has been found to be helpful to estimate the glass transition temperature $T_g$ of the copolymer CP with the aid of the equation from Fox (T. G. Fox, Bull. Am. Phys. Soc. (Ser. II) 1, 123 [1956] and Ullmanns Enzyklopädie der technischen Chemie [Ullmann's Encyclopedia of Industrial Chemistry], Weinheim (1980), pp. 17-18) using the glass transition temperature of the respective homopolymers of the monomers M which constitute the polymer. The latter are known, for example, from Ullmann's Encyclopedia of Industrial Chemistry, VCH, Weinheim, Vol. A 21 (1992) p. 169 or from J. Brandrup, E. H. Immergut, Polymer Handbook 3rd ed., J. Wiley, New York 1989.

Some of the copolymers CP comprised in the preparations according to the invention are known from PCT/EP 04/011797, or they can be prepared by customary methods by radical polymerization of the monomers M. The polymerization can be carried out by free-radical polymerization or by controlled radical polymerization methods. The polymerization can be carried out using one or more initiators and can be carried out as solution polymerization, as emulsion polymerization, as suspension polymerization or as precipitation polymerization, or else neat. The polymerization can be carried out as a batch reaction or in semicontinuous or continuous operation.

The reaction times are generally in the range from 1 to 12 hours. The temperature range in which the reactions may be carried out is generally from 20 to 200° C., preferably from 40 to 120° C. The polymerization pressure is of minor importance and can be in the range from atmospheric pressure or slightly reduced pressure, for example >800 mbar, or at superatmospheric pressure, for example up to 10 bar, it also being possible to use higher or lower pressures.

Suitable initiators for the radical polymerization are customary radical-forming substances. Preference is given to initiators from the group of the azo compounds, the peroxide compounds or the hydroperoxide compounds. Examples which may be mentioned are acetyl peroxide, benzoyl peroxide, lauroyl peroxide, tert-butylperoxy isobutyrate, caproyl peroxide, cumene hydroperoxide, 2,2'-azobisisobutyronitrile, 2,2'-azobis(2-methylbutyronitrile), 2,2'-azobis[2-methyl-N-(2-hydroxyethyl)propionamide], 1,1'-azobis(1-cyclohexanecarbonitrile), 2,2'-azobis(2,4-dimethylvaleronitrile), 2,2'-azobis(N,N'-dimethyleneisobutyroamidine). Particular preference is given to azobisisobutyronitrile (AIBN). The initiator is usually employed in an amount of from 0.02 to 5% by weight and in particular from 0.05 to 3% by weight, based on the amount of monomers M. The optimum amount of initiator depends, of course, on the initiator system used and can be determined in standard experiments by the person skilled in the art. Some or all of the initiator may be initially charged in the reaction vessel. Preferably, the major amount of the initiator, in particular at least 80%, for example from 80 to 100%, of the initiator, is added into the polymerization reactor during the course of the polymerization.

Of course, the molecular weight of the copolymers CP can be adjusted by adding a small amount of regulators, for example from 0.01 to 5% by weight, based on the monomers M being polymerized. Suitable regulators are in particular organic thio compounds, for example mercaptoalcohols, such as mercaptoethanol, mercaptocarboxylic acids, such as thioglycolic acid, mercaptopropionic acid, alkylmercaptans, such as dodecylmercaptan, furthermore allyl alcohols and aldehydes.

The copolymers CP are prepared, in particular, by radical solution polymerization in a solvent. Examples of solvents are water, alcohols, such as, for example, methanol, ethanol, n-propanol and isopropanol, dipolar-aprotic solvents, for example N-alkyllactams, such as N-methylpyrrolidone (NMP), N-ethylpyrrolidone, furthermore dimethyl sulfoxide (DMSO), N,N-dialkylamides of aliphatic carboxylic acids, such as N,N-dimethylformamide (DMF), N,N-dimethylacetamide, furthermore aromatic, aliphatic and cycloaliphatic hydrocarbons which may be halogenated, such as hexane, chlorobenzene, toluene or benzene. Preferred solvents are isopropanol, methanol, toluene, DMF, NMP, DMSO and hexane; particular preference is given to DMF.

The preparations according to the invention can be formulated in solid form or in liquid form. Depending on the embodiment, the preparations according to the invention may also comprise auxiliaries and/or carriers customary in crop protection compositions or in compositions for the protection of materials. The auxiliaries include in particular conventional surface-active substances and other additives and carriers customary in crop protection and in the protection of materials, which compounds may be solid or liquid. The surface-active substances include in particular surfactants, especially those having wetting agent properties. The other auxiliaries (additives) include in particular thickeners, antifoams, preservatives, antifreeze agents, stabilizers, anticaking agents or powder-flow aids and buffers.

Conventional surface-active substances which are suitable in principle are anionic, nonionic and amphoteric surfactants including polymer surfactants, and the molecular weight of the surfactants will typically not exceed a value of 2000 Dalton and in particular 1000 Dalton (number-average).

The anionic surfactants include, for example, carboxylates, in particular alkali metal, alkaline earth metal, and ammonium salts of fatty acids, for example potassium stearate, which are usually also referred to as soaps; acyl glutamates; sarcosinates, for example sodium lauroyl sarcosinate; taurates; methylcelluloses; alkyl phosphates, in particular alkyl esters of mono- and diphosphoric acid; sulfates, in particular alkyl sulfates and alkyl ether sulfates; sulfonates, furthermore alkyl sulfonates and alkylaryl sulfonates, in particular alkali metal, alkaline earth metal and ammonium salts of arylsulfonic acids and of alkyl-substituted arylsulfonic acids, alkylbenzenesulfonic acids, such as, for example, lignol and phenolsulfonic acid, naphthalene- and dibutylnaphthalenesulfonic acids, or dodecylbenzenesulfonates, alkylnaphthalene-sulfonates, alkyl methyl ester sulfonates, condensates of sulfonated naphthalene and derivatives thereof with formaldehyde, condensates of naphthalene sulfonic acids, phenol- and/or phenolsulfonic acids with formaldehyde or with formaldehyde and urea, mono- or dialkyl sulfosuccinates; and also protein hydrolysates and lignosulfite waste liquors. The abovementioned sulfonic acids are advantageously used in the form of their neutral or, if appropriate, basic salts.

The nonionic surfactants include, for example:
fatty alcohol alkoxylates and oxoalcohol alkoxylates, in particular ethoxylates and propoxylates having degrees of alkoxylation of usually from 2 to 100 and in particular from 3 to 50, for example alkoxylates of $C_8$-$C_{30}$-alkanols or alk(adi)enols, for example of isotridecyl alcohol, lauryl alcohol, oleyl alcohol or stearyl alcohol, and their $C_1$-$C_4$-alkyl ethers and $C_1$-$C_4$-alkyl esters, for example their acetates;
alkoxylated animal and/or vegetable fats and/or oils, for example corn oil ethoxylates, castor oil ethoxylates, tallow fat ethoxylates,
glycerol esters, such as, for example, glycerol monostearate,
alkylphenol alkoxylates, such as, for example, ethoxylated isooctylphenol, octylphenol or nonylphenol, tributylphenol polyoxyethylene ether,
fatty amine alkoxylates, fatty acid amide alkoxylates and fatty acid diethanolamide alkoxylates, in particular their ethoxylates,
sugar surfactants, sorbitol esters, such as, for example, sorbitan fatty acid esters (sorbitan monooleate, sorbitan tristearate), polyoxyethylene sorbitan fatty acid esters, alkyl polyglycosides, N-alkylgluconamides,
alkyl methyl sulfoxides,
alkyldimethylphosphine oxides, such as, for example, tetradecyldimethylphosphine oxide.

The amphoteric surfactants include, for example, sulfobetaines, carboxybetaines and alkyldimethylamine oxides, for example tetradecyldimethylamine oxide.

Other surfactants which may be mentioned here by way of example are perfluoro surfactants, silicone surfactants, phospholipids, such as, for example, lecithin or chemically modified lecithins, amino acid surfactants, for example N-lauroylglutamate.

Unless specified otherwise, the alkyl chains of the surfactants listed above are linear or branched radicals having usually from 6 to 30 and in particular from 8 to 20 carbon atoms.

In one embodiment, the aqueous preparations according to the invention comprise not more than 10% by weight, preferably not more than 5% by weight and in particular not more than 3% by weight, for example from 0.01 to 5% by weight or from 0.1 to 3% by weight, of conventional surface-active substances, in each case based on the total amount of active compound and copolymer CP.

However, depending on the application, it may be advantageous to formulate the active compound preparations according to the invention with surface-active substances. In this case, the proportion of conventional surface-active substance is frequently in the range from 0.1 to 60% by weight, in particular in the range from 0.5 to 50% by weight, based on the total amount of active compound and copolymer CP, or in the range from 0.1 to 60% by weight, in particular in the range from 0.5 to 50% by weight and especially in the range from 0.5 to 30% by weight, based on the total weight of the formulated preparation.

In spite of the fact that one of the advantages of the preparations according to the invention is their low content of volatile organic compounds, for some applications it may be desirable for the preparations according to the invention to be mixed with organic solvents, oils and fats, preferably solvents or oils and fats which are environmentally friendly or biocompatible, for example the water-miscible solvents mentioned above or solvents, oils or fats whose miscibility with water is only very limited, or which are immiscible with water. These include, for example:
paraffin oils, aromatic hydrocarbons and mixtures of aromatic hydrocarbons, for example xylenes, Solvesso 100, 150 or 200, and the like,
phenols and alkylphenols, for example phenol, hydroquinone, nonylphenol, etc.,
ketones having more than 4 carbon atoms, such as cyclohexanone, isophorone, isoperone, acetophenone, acetonaphthone,
alcohols having more than 4 carbon atoms, such as acetylated lanolin alcohol, cetyl alcohol, 1-decanol, 1-heptanol, 1-hexanol, isooctadecanol, isopropyl alcohol, oleyl alcohol, benzyl alcohol,
carboxylic esters, for example dialkyl adipates, such as bis(2-ethylhexyl) adipate, dialkyl phthalates, such as bis (2-ethylhexyl) phthalate, alkyl acetates (also branched alkyl groups), such as ethyl acetate and ethyl acetoacetate, stearates, such as butyl stearate, glycerol monostearate, citrates, such as acetyltributyl citrate, furthermore cetyl octanoate, methyl oleate, methyl p-hydroxy benzoate, methyl tetradecanoate, propyl p-hydroxybenzoate, methyl benzoate, lactates, such as isopropyl lactate, butyl lactate and 2-ethylhexyl lactate, vegetable oils, such as palm oil, rapeseed oil, castor oil and derivatives thereof, such as, for example, oxidized, coconut oil, cod liver oil, corn oil, soybean oil, linseed oil, olive oil, peanut oil, safflower oil, sesame seed oil, grapefruit oil, basil oil, apricot oil, ginger oil, geranium oil, orange oil, rosemary oil, macadamia oil, onion oil, mandarin oil, pine oil, sunflower oil, hydrogenated vegetable oils, such as hydrogenated palm oil, hydrogenated rapeseed oil, hydrogenated soybean oil, animal oils, such as pig fat oil, fish oils, dialkylamides of medium- to long-chain fatty acids, for example hallcomides, and also vegetable oil esters, such as rapeseed oil methyl ester.

Suitable thickeners are compounds which confer a pseudoplastic flow behavior to the aqueous preparations, i.e. high viscosity at rest and low viscosity in the agitated state. Mention may be made, in this connection, for example, of polysaccharides, such as xanthan (Kelzane® from Kelco; Rhodopol® 23 from Rhone Poulenc; or Veegum® from R. T. Vanderbilt), and also inorganic sheet minerals, such as Attaclay® (from Engelhardt), xanthan being preferred.

Antifoam agents suitable for the dispersions according to the invention are, for example, silicone emulsions (such as, for example, Silikon® SRE, from Wacker, or Rhodorsil® from Rhodia), long-chain alcohols, fatty acids, organofluorene compounds and mixtures thereof.

Bactericides can be added to stabilize the preparations according to the invention against attack by microorganisms. These are typically isothiazolone compounds, for example 1,2-benzisothiazolin-3-one, 5-chloro-2-methylisothiazol-3-one, 2-methyl-isothiazol-3-one or 2-octylisothiazol-3-one, which are available for example under the trade names Proxel® from Arch Chemical Inc., Acticide® RS from Thor Chemie and Kathon® MK from Rohm & Haas.

Suitable antifreeze agents are organic polyols, for example ethylene glycol, propylene glycol or glycerol. These are employed in aqueous formulations, usually in amounts of not more than 20% by weight, for example from 1 to 20% by weight and in particular from 2 to 10% by weight, based on the total weight of the aqueous active compound preparation.

If appropriate, the active compound preparations according to the invention may comprise from 1 to 5% by weight of buffer, based on the total amount of the preparation produced, to regulate the pH of the preparation or the dilute application form, the amount and type of buffer used depending on the chemical properties and the amount of active compounds and the polymer CP. Examples of buffers are alkali metal salts of weak inorganic or organic acids, such as, for example, phosphoric acid, boric acid, acetic acid, propionic acid, citric acid, fumaric acid, tartaric acid, oxalic acid and succinic acid.

Examples of powder-flow aids are in particular silicic acid, especially fumed silicic acid and precipitated silicic acid, and also calcium carbonate and magnesium stearate. The amount of powder-flow aid, if present, is typically up to 5% by weight, in particular up to 2% by weight, for example from 0.1 to 5% by weight or from 0.2 to 2% by weight, based on the total weight of the composition.

Suitable carriers are, in principle, all liquid and solid substances which are usually employed in formulations for crop protection or the protection of materials, in particular in formulations of fungicides, and which are typically chemically inert. Liquid carriers are in particular water and mixtures of water with organic water-miscible solvents. Solid carriers are, for example, silicates and alumosilicates including bole, loess, clays and aluminas, for example phyllosilicates and tectosilicates, such as montmorillonite, hectorite, saponite, beidellite, sauconite, bentonite, talcum, kaolin, attapulgite, furthermore amorphous silicates and silicic acids, such as silica gels, kieselguhr, for example in the form of diatomaceous earth, precipitated silicic acid, synthetic silicates and alumosilicates, such as zeolites, furthermore limestone, lime, chalk, dolomite, calcium sulfate and magnesium sulfate, magnesium oxide, ground synthetic materials, fertilizers, such as, for example, ammonium sulfate, ammonium phosphate, ammonium nitrate, ureas and products of vegetable origin, such as cereal meal, tree bark meal, wood meal and nutshell meal, cellulose powder and other solid carriers. The solid carriers are preferably water-soluble or water-dispersible.

A further preferred embodiment of the invention relates to preparations in solid form. The total amount of active compound (active compound 1+active compound 2) is generally in the range from 5 to 90% by weight, in particular from 10 to 70% by weight and especially from 15 to 60% by weight, based on the total weight of the preparation. The proportion of copolymer CP is usually from 5 to 95% by weight, in particular from 10 to 90% by weight and especially from 20 to 85% by weight, based on the total weight of the preparation. The proportion of auxiliaries and solid carriers may be up to 90% by weight, in particular up to 80% by weight and especially up to 65% by weight of the solid preparation according to the invention. It is to be understood that, in the solid formulations, the proportion of liquid components different from active compounds 1 and 2, in particular liquid solvent components, is generally not more than 20% by weight of the formulation, in particular not more than 10% by weight and especially not more than 1% by weight.

The solid preparations may be present in various macroscopic forms. Examples of macroscopic forms which may be mentioned are powders as obtained, for example, by spray drying or freeze drying of liquid formulations, ground materials, granules, agglomerates or else films. Preference is given to powders.

A first embodiment of solid preparations are those which substantially do not comprise any solid carrier and which substantially, i.e. to at least 95% and in particular to at least 99%, consist of active compounds 1 and 2, polymer CP and, if appropriate, solid, preferably water-soluble auxiliaries. In these formulations, the total amount of active compound (active compound 1+active compound 2) is generally in the range from 5 to 90% by weight, in particular from 10 to 70% by weight and especially from 15 to 60% by weight, based on the total weight of the preparation. The proportion of copolymer CP is usually from 5 to 95% by weight, in particular from 10 to 90% by weight and especially from 20 to 85% by weight, based on the total weight of the solid carrier-free preparation. The proportion of auxiliaries may be up to 60% by weight, in particular up to 80% by weight and especially up to 65% by weight of the solid preparation according to the invention. If the solid preparations are present as powders, they may comprise a powder-flow aid in the amounts mentioned above. The proportion of solid inert carriers is preferably not more than 5% by weight, in particular not more than 1% by weight.

A second embodiment of solid preparations are those which, in addition to the active compounds 1 and 2, the polymer CP and, if appropriate, solid, preferably water-soluble auxiliaries, comprise at least one solid carrier. In these formulations, the total amount of active compound (active compound 1+active compound 2) is generally in the range from 5 to 80% by weight, in particular from 10 to 60% by weight and especially from 15 to 50% by weight, based on the total weight of the preparation. The proportion of copolymer CP is usually from 5 to 85% by weight, in particular from 10 to 70% by weight and especially from 20 to 65% by weight, based on the total weight of the solid carrier-free preparation. The proportion of carrier material is typically from 10 to 90% by weight, from 20 to 80% by weight and in particular from 30 to 65% by weight, based on the total weight of the composition. The proportion of auxiliaries may be up to 80% by weight, in particular up to 70% by weight and especially up to 55% by weight of the solid preparation according to the invention. If the solid preparations are present as powders, they may comprise a powder-flow aid in the amounts mentioned above. Preferred carrier materials are silicates, for example phyllosilicates including clays, such as montmorillonite, hectorite, saponite, beidellite, sauconite, bentonite, talcum, furthermore amorphous silicates and silicic acids, such as silica gels, kieselguhr, for example in the form of diatomaceous earth, precipitated silicic acid, synthetic silicates, such as zeolites.

In another embodiment, the preparation according to the invention is a liquid or, in particular, an aqueous preparation. In addition to the components active compound 1, active compound 2 and copolymer CP, such preparations also comprise a liquid carrier, in particular water or a mixture of water with a water-miscible organic solvent, the proportion of organic solvents preferably not exceeding 20% by weight, based on the total weight of the composition.

Examples of water-miscible organic solvents are $C_3$-$C_4$-ketones, such as acetone and methyl ethyl ketone, cyclic ethers, such as dioxane and tetrahydrofuran, $C_1$-$C_4$-alkanols, such as methanol, ethanol, n-propanol, isopropanol, n-butanol, tert-butanol, polyols and their mono- and dimethyl ethers, such as glycol, propanediol, ethylene glycol monomethyl ether, diethylene glycol, diethylene glycol monomethyl ether, diethylene glycol dimethyl ether, glycerol, furthermore $C_2$-$C_3$-nitriles such as acetonitrile and propionitrile, dimethyl sulfoxide, dimethylformamide, formamide, acetamide, dimethylacetamide, butyrolactone, 2-pyrrolidone and N-methylpyrrolidone.

The total amount of active compound (active compound 1+active compound 2) present in the liquid, in particular aqueous concentrates (liquid formulations) is generally in the range from 1 to 50% by weight, in particular from 5 to 40% by weight and especially from 7 to 35% by weight, based on the total weight of the preparation. The amount of copolymer CP is usually from 3 to 50% by weight, in particular from 5 to 45% by weight and especially from 10 to 40% by weight, based on the total weight of the preparation. The proportion of auxiliaries may be up to 30% by weight, in particular up to 20% by weight and especially up to 10% by weight of the liquid preparation according to the invention. Typical auxiliaries of liquid preparations are, for example, thickeners, antifoams, preservatives, antifreeze agents, biocides, pH-adjusting agents and surface-active substances. The solids content is typically in the range from 5 to 70% by weight, in particular from 10 to 60% by weight and especially from 20 to 55% by weight. The proportion of water-immiscible volatile components is advantageously not more than 5% by weight, in particular not more than 1% by weight, based on the total weight of the aqueous liquid formulation.

In the aqueous preparations, active compounds 1 and 2 and copolymer CP are present in the aqueous phase in finely distributed form. The mean particle size, determined by light scattering, in the concentrates is typically less than 1 μm, in particular less than 500 nm and especially less than 300 nm.

Aqueous phase is understood to be pure water or water which comprises dissolved additives, for example a buffer system or salts or further additives, such as, for example, water-miscible solvents. The pH of the aqueous phase is generally in the range from 2 to 13, preferably from 3 to 12, particularly preferably from 4 to 10.

Typically, the aqueous formulations comprise at least one of the antifreeze agents mentioned above, if appropriate one or more of the biocides mentioned above, if appropriate one or more of the thickeners mentioned above, if appropriate one or more of the agents for adjusting the pH (buffers) mentioned above, if appropriate one or more of the antifoams mentioned above and if appropriate one or more of the surface-active substances mentioned above.

The invention furthermore relates to a process for preparing the preparations described, hereinbelow also referred to as process 1. Typically, this process comprises intimate mixing of the components present in the preparations according to the invention using customary processes.

In a preferred embodiment, intimate mixing is achieved by a process comprising
i) providing a solution of active compound 1, of copolymer CP and of at least one further active compound 2 in an organic solvent and then
ii) substantial or complete removal of the organic solvent.

If, as a result of the preparation, the copolymer CP is already present in an organic solvent, this solution is preferably used for mixing with the active compound or the active compound solution.

In a first step of process 1, a solution of the copolymer and at least one further active compound in a suitable organic solvent is prepared. To this end, a first solution of the copolymer CP in a first organic solvent is generally mixed with one or two separate solutions of the active compounds 1 and 2 in an organic solvent, where the solutions may already comprise further auxiliaries and additives. It is also possible to add the auxiliaries and additives at a later point in time. The solvents used for preparing the solutions may be identical or different; typically, solvents which are miscible with one another will be chosen. It may not be necessary to prepare a solution of copolymer CP if the synthesis of copolymer CP is carried out in a solvent suitable for use in the process for preparing the formulation according to the invention.

Examples of organic solvents suitable for this purpose are $C_1$-$C_6$-alkyl alcohols, such as methanol, ethanol, propanol, isopropanol, 1-butanol, 2-butanol, tert-butanol, esters of aliphatic $C_1$-$C_4$-carboxylic acids with $C_1$-$C_4$-alkanols, such as ethyl acetate, butyl acetate, ketones having preferably 3 to 6 carbon atoms, such as acetone, methyl ethyl ketone, methyl isopropyl ketone, methyl isobutyl ketone, acetals, di-$C_1$-$C_4$-alkyl ethers, such as diethyl ether, methyl tert-butyl ether, cyclic ethers, such as tetrahydrofuran, aliphatic $C_1$-$C_4$-carboxylic acids, such as formic acid, acetic acid, propionic acid, N-substituted or N,N-disubstituted $C_1$-$C_4$-carboxamides, such as acetamide, dimethylformamide (DMF) and dimethylpropionamide, lactams, such as N-methylpyrrolidone, lactones, such as, for example, butyrolactone, aliphatic and aromatic chlorinated hydrocarbons, such as methylene chloride, chloroform, 1,2-dichloroethane or chlorobenzene, and also mixtures of the solvents mentioned. Preferred organic solvents are methanol, ethanol, isopropanol, dimethylformamide, N-methylpyrrolidone, methylene chloride, chloroform, 1,2-dichloroethane, chlorobenzene, acetone, methyl ethyl ketone, methyl isopropyl ketone, methyl isobutyl ketone, tetrahydrofuran and also mixtures of these solvents.

Particularly preferred solvents are methanol, ethanol, isopropanol, dimethylformamide and tetrahydrofuran and mixtures thereof.

In a second step, the solvent(s) is/are very substantially removed in a customary manner by suitable processes. Customary processes for removing solvents are, for example, spray drying, evaporation at reduced pressure, freeze drying, evaporation under atmospheric pressure, if appropriate at elevated temperature. The processes suitable for drying furthermore include lyophilization or drying in a fluidized-bed dryer. This affords the active compound formulations according to the invention in solid form.

In this manner, a solid, viscous or gel-like composition is generally obtained. If a solid is obtained after removal of the solvent, it is possible to prepare in a manner known per se and depending on the drying conditions finely divided powders or coarsely divided granules which can be dispersed or dissolved in water without any problems and without any significant increase of the particle size. It is also possible to prepare a coarsely divided solid and to grind this to the desired particle size.

To prepare a solid formulation which comprises a carrier, it is also possible, for example, to adopt a procedure where
i) one or more separate solutions of the active compound 1, the copolymer CP, the at least one further active compound 2 and, if appropriate, the auxiliaries in one or more different organic solvents are provided,
ii) these solutions are mixed with the carrier or applied to the carrier and
iii) the organic solvent(s) are substantially or completely removed.

This process, hereinbelow also referred to as process 2, is particularly suitable if a viscous or gel-like product is obtained when no carrier is used.

In process 2, the solution(s) are advantageously applied to the carrier by a spray process, for example by a spray drying or spray granulation process, where the solvent(s) is/are at the same time evaporated. The auxiliaries may also be applied to the carrier in this manner or be added at a later point in time.

With respect to the solutions of the active compounds 1 and 2, the copolymer CP and the auxiliaries, in principle, what was said above for process 1 applies analogously.

Typically, the preparation of aqueous preparations according to the invention comprises the active compounds 1 and 2, the copolymer CP and any auxiliaries being incorporated into an aqueous dispersion medium. The process may, for example, comprise the following steps:
i) providing a solution comprising the active compounds 1 and 2, the copolymer CP and, if appropriate, part or all of the auxiliaries in an organic solvent which is preferably miscible with water, a melt of the components mentioned above or a powder of the components mentioned above,
ii) incorporating the solution, the melt or the powder into an aqueous dispersion medium and
iii) if present, substantial or complete removal of the organic solvent.

To prepare the aqueous preparations according to the invention, the solution or melt or the powder obtained in step i) will be dispersed either in water or in an aqueous medium. An aqueous medium is to be understood as meaning water, an aqueous solution of surface-active substances and also mixtures of water with organic water-miscible solvents, where the proportion of such solvents is typically not more than 20% by volume, based on the total amount of water and solvent.

Dispersing is usually carried out by application of shear forces, for example by shaking at high frequencies and high amplitudes or by stirring at high frequencies, by turbine agitation, or by use of a mixing chamber. Dispersing can be carried out continuously or batchwise. Preference is given to continuous dispersion. Dispersing can, if appropriate, be carried out at elevated temperature and/or elevated pressure.

The organic solvent used for preparing the solution is preferably miscible with water. In this context, miscible with water means that, under the mixing conditions, the organic solvents are, without phase separation, miscible with water by at least 10% by weight, preferably 15% by weight, particularly preferably 20% by weight. Examples of water-miscible organic solvents are those mentioned above, in particular cyclic ethers, such as tetrahydrofuran.

If a solution of the active compounds 1 and 2 and the copolymer CP has been dispersed in water, the organic solvent will then be substantially or completely removed. This is typically carried out by distillation, water that has been distilled off usually being successively replaced.

In another, likewise preferred process, the preparation of aqueous preparations according to the invention comprises the following steps:
i) providing an aqueous solution comprising the copolymer CP,
ii) providing one or two separate solutions comprising active compound 1 and the at least one further active compound 2 in one or more water-miscible organic solvents,
iii) mixing of the aqueous solution of the copolymer CP with the solution(s) of active compounds 1 and 2, and
iv) substantial or complete removal of the organic solvent(s).

In a first step, the copolymer CP and, if appropriate, further additives are dissolved in an aqueous solvent system. If the preparation already affords an aqueous solution of the copolymer, this aqueous solution is preferably used for mixing with the active compound solution. Furthermore, active compound 1 and active compound 2 are dissolved in a water-miscible solvent, if appropriate with addition of further auxiliaries. The aqueous solution of the copolymer CP is then mixed with the solution of epoxiconazole and the active compound 2.

Mixing is advantageously carried out with input of energy, such as, for example, by application of shear forces, by shaking at high frequencies and high amplitudes or by stirring at high frequencies, by turbine agitation or by use of a mixing chamber. Mixing can be carried out continuously or batchwise. Preference is given to continuous mixing. The solvents of the dispersion obtained in this manner can be removed in a customary manner, as illustrated above.

The preparations according to the invention are distinguished firstly by the fact that an extremely fine division of the dispersed active compound phase is ensured on dilution with water, where the mean particle size of the dispersed active compound phase is in the ranges mentioned above. Even on prolonged storage and/or storage at elevated temperature, the active compound preparations according to the invention do not lose these properties. The use of further surface-active compounds for this purpose is not required. Moreover, the preparations according to the invention can be formulated as low-solvent preparations (solvent content <5% by weight) or as solvent-free preparations (solvent content <1% by weight, in particular <0.5% by weight). Without any separation taking place, the preparations can be stored over a relatively long period of time of several months, even at elevated temperature and/or at highly fluctuating temperatures. Also, crystallization phenomena like those that may sometimes occur with formulations of some conazole fungicides and in particular epoxiconazole formulations do not take place.

The preparations according to the invention are particularly suitable for controlling phytopathogenic fungi and, in this respect, are at least equal and frequently superior to customary formulations of active compounds 1 and 2. The preparations according to the invention are highly effective against a broad spectrum of phytopathogenic fungi, in particular from the classes of the Ascomycetes, Deuteromycetes and Basidiomycetes.

They are particularly important in the control of a multitude of fungi on various cultivated plants, such as wheat, rye, barley, oats, rice, corn, grass, bananas, cotton, soybeans, coffee, sugar cane, vines, fruits, ornamental plants, and vegetables, such as cucumbers, beans, tomatoes, potatoes and cucurbits and the seeds of these plants.

They are especially suitable for controlling the following plant diseases:
- *Alternaria* species on vegetables and fruit,
- *Bipolaris* and *Drechslera* species on cereals, rice and lawns,
- *Blumeria graminis* (powdery mildew) on cereals,
- *Botrytis cinerea* (gray mold) on strawberries, vegetables, ornamental plants and grapevines,
- *Erysiphe cichoracearum* and *Sphaerotheca fuliginea* on cucurbits,
- *Fusarium* and *Verticillium* species on various plants,
- *Mycosphaerella* species on cereals, bananas and peanuts,
- *Phytophthora infestans* on potatoes and tomatoes,
- *Plasmopara viticola* on grapevines,
- *Podosphaera leucotricha* on apples,
- *Pseudocercosporella herpotrichoides* on wheat and barley,
- *Pseudoperonospora* species on hops and cucumbers,
- *Puccinia* species on cereals,
- *Pyricularia oryzae* on rice,
- *Rhizoctonia* species on cotton, rice and lawns,
- *Septoria tritici* and *Stagonospora nodorum* on wheat,
- *Uncinula necator* on grapevines,
- *Ustilago* species on cereals and sugar cane, and also
- *Venturia* species (scab) on apples and pears.

The preparations according to the invention are also suitable for controlling harmful fungi, such as *Paecilomyces variotti*, in the protection of materials (for example wood, paper, paint dispersions, fibers or fabrics) and in the protection of stored products.

The preparations are typically applied by treating the fungi or the plants, seeds, materials or soil to be protected from fungal attack with a dilute aqueous preparation of the preparations according to the invention comprising a fungicidally effective amount of the active compounds 1 and 2. The application can be carried out both before and after the infection of the materials, plants or seeds by the fungi.

The active compound concentrations in the aqueous preparations may be varied within relatively large ranges. In general, they are between 0.0001 and 1%, preferably between 0.0005 and 0.1%.

When employed in crop protection, the application rates are between 0.01 and 2.0 kg of active compound per ha, depending on the kind of effect desired.

In seed treatment, amounts of active compound of from 1 to 1000 g/100 kg of seed, preferably from 1 to 200 g/100 kg, in particular from 5 to 100 g/100 kg are generally used.

When used in the protection of materials or stored products, the amount of active compound applied depends on the kind of application area and on the desired effect. Amounts customarily applied in the protection of materials are, for example, from 0.001 g to 2 kg, preferably from 0.005 g to 1 kg, of active compound per cubic meter of treated material.

The examples below serve to illustrate the invention and are not to be understood as limiting it.

Analysis:

The glass transition temperature was determined using a DSC apparatus DSC30 from Mettler at a heating rate of 10 K/min.

The molecular weights were determined by gel permeation chromatography (instrument "Series 1100" from Agilent) using an RI detector and a 5μ mixed-D column from PL at 30° C. (column temperature). The mobile phase used was dimethylformamide, which comprised 0.5% lithium bromide. The flow rate was 1 ml/min. Calibration was carried out using polymethyl methacrylate calibration sets.

PREPARATION OF THE COPOLYMERS CP

Preparation Example 1

Copolymer CP1

250 g of DMF were initially charged in a reaction vessel and heated to 90° C. Over a period of 3 h, feed 1, consisting of 49.5 g of 2-acrylamido-2-methylpropanesulfonic acid, 96.1 g of 2-hydroxyethyl acrylate, 145.6 g of n-butyl acrylate and 148.5 g of DMF, and feed 2, consisting of 8.74 g of AIBN and 301.5 g of DMF, were added in parallel, at the same temperature. After the feeds had ended, the mixture was polymerized at 95° C. for a further 2 h.

Preparation Example 2

Copolymer CP2

300 g of DMF were initially charged in a reaction vessel and heated to 90° C. Over a period of 3 h, feed 1, consisting of 36.0 g of 2-acrylamido-2-methylpropanesulfonic acid, 184.0 g of 2-hydroxyethyl acrylate, 180.0 g of n-butyl acrylate and 148.5 g of DMF, and feed 2, consisting of 12.0 g of AIBN and 120 g of DMF, were added in parallel, at the same temperature. After the feeds had ended, the mixture was polymerized at 95° C. for a further 2 h.

Preparation Example 3

Copolymer CP3

Under inert gas, 300 g of DMF were initially charged in a reaction vessel and heated to 90° C. Over a period of 3 h, feed 1, consisting of 36.0 g of 2-acrylamido-2-methylpropanesulfonic acid, 192.0 g of 2-hydroxyethyl acrylate, 172.0 g of n-butyl acrylate and 148.5 g of DMF, and feed 2, consisting of 12.0 g of AIBN and 120 g of DMF, were added in parallel, at the same temperature. After the feeds had ended, the mixture was polymerized at 95° C. for a further 2 h.

Preparation Examples 4 to 6

General Preparation Procedure

In a synthesis reactor AutoPlant A100 from Chemspeed®, 15 ml of DMF per reaction vessel were initially charged and heated to 95° C. With stirring and with the temperature being maintained, feed 1 and—starting at the same time as feed 1-feed 2 were added in parallel over 180 min and 195 min, respectively. After the feeds had ended, the mixture was post-polymerized at 95° C. for a further 60 min.

Preparation Example 4

Copolymer CP4

Feed 1: Mixture comprising 10.5 g of methyl methacrylate, 3.5 g of lauryl acrylate and 7.0 g of 2-acrylamido-2-methylpropanesulfonic acid, dissolved in DMF to 49 ml.
Feed 2: 0.63 g of 2,2'-azobis(2-methylpropionitrile) dissolved in DMF to 6 ml.

Preparation Example 5

Copolymer CP5

Feed 1: Mixture comprising 10.5 g of n-butyl acrylate, 7.0 g of 2-hydroxyethyl acrylate and 3.5 g of 2-acrylamido-2-methylpropanesulfonic acid, dissolved in DMF to 49 ml.
Feed 2: 0.63 g of 2,2'-azobis(2-methylpropionitrile) dissolved in DMF to 6 ml.

Preparation Example 6

Copolymer CP6

Feed 1: Mixture comprising 17.5 g of methyl acrylate and 3.5 g of 2-acrylamido-2-methylpropanesulfonic acid, dissolved in DMF to 49 ml.
Feed 2: 0.63 g of 2,2'-azobis(2-methylpropionitrile) dissolved in DMF to 6 ml.

Preparation Examples 7 to 9

General Preparation Procedure

In a synthesis reactor Accelerator™ SLT100 from Chemspeed®, per reaction vessel 0.21 ml of initiator solution 2 was added to 6.72 ml of monomer solution 1. With shaking, the mixture was then heated at 95° C. for 4 h, a further 0.07 ml of initiator solution 2 was then added and the polymerization was concluded at 95° C. over a period of 2 h.

Preparation Example 7

CP7

Monomer solution 1: Mixture comprising 150 mg of methyl methacrylate, 450 mg of 2-phenoxyethyl acrylate and 300 mg of 2-acrylamido-2-methylpropanesulfonic acid dissolved in DMF to 8.64 ml.
Initiator solution 2: 100 mg of 2,2'-azobis(2-methylpropionitrile) dissolved in DMF to 1.00 ml.

Preparation Example 8

CP8

Monomer solution 1: Mixture comprising 300 mg of hydroxypropyl methacrylate, 300 mg of styrene and 300 mg of 2-acrylamido-2-methylpropanesulfonic acid dissolved in DMF to 8.64 ml.
Initiator solution 2: 100 mg of 2,2'-azobis(2-methylpropionitrile) dissolved in DMF to 1.00 ml.

Preparation Example 9

CP9

Monomer solution 1: Mixture comprising 450 mg of methyl acrylate, 300 mg of 1-vinyl-2-pyrrolidone and 150 mg of 2-acrylamido-2-methylpropanesulfonic acid dissolved in DMF to 8.64 ml.
Initiator solution 2: 100 mg of 2,2'-azobis(2-methylpropionitrile) dissolved in DMF to 1.00 ml.

Molecular weights and glass temperatures of copolymers CP1 to CP4 are listed in table 1:

TABLE 1

| Copolymer | $M_n$ | $M_w$ | $T_g$ [° C.] |
|---|---|---|---|
| CP1 | 5700 | 11 000 | 16 |
| CP2 | 7600 | 15 900 | −6 |
| CP3 | 7800 | 16 800 | −4 |
| CP4 | 12 437 | 21 853 | n.d. | n.d. not determined

Preparation of Preparations Z1, Z2, Z3, Z4 and Z5 According to the Invention:
General Preparation Procedure for Solid Formulations 10 g of an active compound mixture of epoxiconazole and pyraclostrobin (weight ratio 5:7 in the case of Z1, Z2 and Z3; weight ratio 1:1 in the case of Z5) or epoxiconazole and metconazole (weight ratio 1:1 in the case of Z4) were dissolved in a solution of 30 g of copolymer CP and 70 g of DMF. The solvent was removed under reduced pressure at a temperature of 80° C., giving a solid homogeneous material which had no crystalline components.

In comparative experiments VZ1, VZ2, VZ3 and VZ4, instead of the active compound mixture 10 g of pure epoxiconazole were formulated under the conditions given above. This gave solid materials each having crystalline components.

TABLE 2

Preparations of the solid active compound formulations

| Preparation | Copolymer | Type of active compound | Active compound/copolymer [g/g][1) |
|---|---|---|---|
| Z1 | CP1 | epoxiconazole/pyraclostrobin 5:7[1) | 1:3 |
| Z2 | CP2 | epoxiconazole/pyraclostrobin 5:7[1) | 1:3 |
| Z3 | CP3 | epoxiconazole/pyraclostrobin 5:7[1) | 1:3 |
| Z4 | CP4 | epoxiconazole/metconazole 1:1[1) | 1:3 |
| Z5 | CP4 | metconazole/pyraclostrobin 1:1[1) | 1:3 |
| VZ1* | CP1 | epoxiconazole | 1:3 |
| VZ2* | CP2 | epoxiconazole | 1:3 |
| VZ3* | CP3 | epoxiconazole | 1:3 |
| VZ4* | CP4 | epoxiconazole | 1:3 |

*Comparative formulation
[1)weight ratio

On dilution of the preparations Z1, Z2, Z3, Z4 and Z5 with water to an active compound concentration of 64 ppm, optically water-clear solutions were obtained. Accordingly, the mean particle size of all samples was less than 100 nm. In contrast, on dilution of the samples VZ1 to VZ4, the separation of solid was observed.

To determine the storage stability, samples of preparations Z1, Z2, Z3, Z4 and Z5 were stored for 5 months at −10° C., room temperature or 55° C. In none of the samples was there any formation of crystalline material. After this period of time, all samples could be diluted with water to give optically water-clear solutions.

Application Tests

Examination of the Fungicidal Action

The active compound preparation in question was prepared as a stock solution having a concentration of 64 ppm of active compound and then diluted with water to the active compound concentration stated below (table 3).

Leaves of potted wheat seedlings of the cultivar "Kanzler" were inoculated with a spore suspension of brown rust (*Puccinia recondita*). The pots were then placed in a chamber with high atmospheric humidity (90 to 95%) and at 20 to 22° C. for 24 hours. During this time, the spores germinated and the germ tubes penetrated into the leaf tissue. The next day, the infected plants were sprayed to runoff point with an aqueous suspension having the active compound concentration stated below. The suspension was prepared as described above. After the spray coating had dried, the test plants were cultivated in a greenhouse at temperatures between 20 and 22° C. and at 65 to 70% relative atmospheric humidity for 7 days. The extent of the rust fungus development on the leaves was then determined.

The results of the biological test are summarized in table 3. The results show that, at low application rates, the copolymer-stabilized active compound mixture has better fungicidal activity than commercial products.

TABLE 3

| Preparation: Application rate [ppm] | Infection [%] Z1 | Infection [%] Z2 | Infection [%] Z3 | Infection [%] Conventional suspoemulsion[1] |
|---|---|---|---|---|
| 32 | 2 | 4 | 0 | 6 |
| 16 | 15 | 18 | 6 | 16 |
| 8 | 43 | 40 | 43 | 60 |

[1]Preparation of the conventional suspoemulsion:
4.7% by weight of epoxiconazole
12.5% by weight of pyraclostrobin
29.2% by weight of aromatic solvents
about 12% by weight of fatty alcohol ethoxylate
about 4% by weight of phenolsulfonic acid/formaldehyde condensate sodium salt thickener biocide in 1 l of aqueous formulation

The invention claimed is:

1. A preparation, comprising a mixture of at least two different crop protection agents, where
    a) at least one fungicidally active compound is selected from the group of the conazoles as active compound 1 and
    b) at least one further crop protection agent as active compound 2, and having a solubility in water at 20° C. of less than 20 g/l, furthermore comprising
    c) at least one copolymer CP constructed of ethylenically unsaturated monomers M, where the monomers M comprise
        α) at least one monoethylenically unsaturated monomer M1 which has at least one sulfonic acid group, and
        β) at least one neutral monoethylenically unsaturated monomer M2,
    where the ratio of active compound 1 to active compound 2 is in the range from 1:10 to 10:1,
    where the active compound 2 is selected from the group consisting of conazole fungicides different from active compound 1, strobilurins, morpholine fungicides, spiroxamine, chlorothalonil, metrafenone and boscalid,
    where the monomers M2 comprise at least one monomer M2a which has a solubility in water at 20° C. of less than 50 g/l,
    where in copolymer CP the monomers M1 make up 1 to 90% by weight of the total amount of the monomers M which constitute the copolymer CP and the monomers M2a make up 10 to 99% by weight of the total amount of the monomers M which constitute the copolymer CP.

2. The preparation according to claim 1, in which the active compound 1 is epoxiconazole.

3. The preparation according to claim 2, where the active compound 1 is epoxiconazole and the active compound 2 is pyraclostrobin.

4. The preparation according to claim 2, where the active compound 1 is epoxiconazole and the active compound 2 is selected from the group consisting of prochloraz, cyproconazole, fluquinconazole, hexaconazole, metconazole, penconazole, propiconazole, prothioconazole, tebuconazole and triticonazole.

5. The preparation according to claim 1 in which the monomers M1 are selected from monomers of the formula I

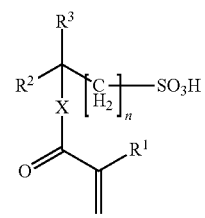

in which
n is 0, 1, 2 or 3;
X is O or $NR^5$;
$R^1$ is hydrogen or methyl;
$R^2$, $R^3$ independently of one another are hydrogen or $C_1$-$C_4$-alkyl and
$R^5$ is hydrogen or $C_1$-$C_4$-alkyl.

6. The preparation according to claim 1 where the monomers M2a are selected from the group consisting of vinylaromatic monomers, esters of acrylic acid with $C_2$-$C_{20}$-alkanols, $C_4$-$C_{10}$-cycloalkanols, phenyl-$C_1$-$C_4$-alkanols and phenoxy-$C_1$-$C_4$-alkanols and the esters of methacrylic acid with $C_1$-$C_{20}$-alkanols, $C_4$-$C_{10}$-cycloalkanols, phenyl-$C_1$-$C_4$-alkanols and phenoxy-$C_1$-$C_4$-alkanols.

7. The preparation according to claim 1 where in copolymer CP the monomers M2 additionally comprise at least one monomer M2b which has a solubility in water at 20° C. of more than 50 g/l.

8. The preparation according to claim 7 where the total amount of the monomers M1+M2b makes up 10 to 90% by weight of the total amount of the monomers M which constitute the copolymer CP.

9. The preparation according to claim 7 where the monomers M2b are selected from the group consisting of hydroxy-$C_2$-$C_4$-alkyl esters of acrylic acid and of methacrylic acid, acrylamide, methacrylamide, acrylonitrile, N-vinyllactams and methyl acrylate.

10. The preparation according to claim 1 where the monomers M2a comprise at least one first monomer M2a(1) having a solubility in water at 20° C. of from 1 to <50 g/l and at least one second monomer M2a(2) having a solubility in water at 20° C. of <1 g/l.

11. The preparation according to claim 10 where the monomers M2a(1) are selected from the group consisting of esters of acrylic acid with $C_2$-$C_4$-alkanols and esters of methacrylic acid with $C_1$-$C_4$-alkanols.

12. The preparation according to claim 10 where the monomers M2a(2) are selected from the group consisting of $C_6$-$C_{20}$-alkyl acrylates and $C_6$-$C_{20}$-alkyl methacrylates.

13. The preparation according to claim 10, wherein the monomers M comprise:
 from 1 to 89% by weight of monomers M1,
 from 10 to 98% by weight of monomers M2a(1) and
 from 1 to 89% by weight of monomers M2a(2),
 all statements in % by weight being based on the total amount of monomers M constituting the copolymer CP.

14. The preparation according to claim 1 in which the copolymer CP has a number-average molecular weight in the range from 1000 to 100 000 Dalton.

15. The preparation according to claim 1 which comprises the copolymer CP in an amount of from 10 to 1000% by weight, based on the total amount of active compound 1 and active compound 2.

16. The preparation according to claim 1 in solid form.

17. The preparation according to claim 16 in the form of a water-dispersible powder or in the form of water-dispersible granules.

18. The preparation according to claim 12, additionally comprising an inert finely divided inorganic carrier.

19. A process for producing a preparation according to claim 1, which comprises intimately mixing active compound 1, copolymer CP and active compound 2 and, optionally, further components.

20. The process according to claim 19 where the mixing comprises the following steps:
 i) providing a solution of active compound 1, copolymer CP and active compound 2 in an organic solvent and
 ii) removing the organic solvent.

21. The process according to claim 20, additionally comprising the dispersion of the material obtained in step ii) or solution obtained in step i) in water.

22. A method of controlling phytopathogenic fungi, comprising the step of:
 applying the preparation according to claim 1 to crops.

* * * * *